United States Patent
Tyagi et al.

(10) Patent No.: US 9,945,785 B2
(45) Date of Patent: Apr. 17, 2018

(54) FLEXIBLE SERS SUBSTRATES WITH FILTERING CAPABILITIES

(71) Applicants: Som Tyagi, Garnet Valley, PA (US); Manuel Figueroa, Philadelphia, PA (US)

(72) Inventors: Som Tyagi, Garnet Valley, PA (US); Manuel Figueroa, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 136 days.

(21) Appl. No.: 15/007,417

(22) Filed: Jan. 27, 2016

(65) Prior Publication Data

US 2016/0161414 A1 Jun. 9, 2016

Related U.S. Application Data

(62) Division of application No. 13/480,778, filed on May 25, 2012, now Pat. No. 9,278,855.

(Continued)

(51) Int. Cl.
*G01J 3/44* (2006.01)
*G01N 21/65* (2006.01)
(Continued)

(52) U.S. Cl.
CPC .......... *G01N 21/658* (2013.01); *B05D 5/061* (2013.01); *B82Y 20/00* (2013.01); *G01N 21/65* (2013.01); *G01N 2021/651* (2013.01)

(58) Field of Classification Search
CPC .......... G01J 3/44; G01N 21/65; G01N 21/64; G01N 21/658; G01N 2021/656; B05D 5/06
See application file for complete search history.

(56) References Cited

U.S. PATENT DOCUMENTS 5,621,522 A * 4/1997 Ewing .................... G01N 21/65
356/301
6,770,488 B1 * 8/2004 Carron ................. G01N 21/658
356/301

(Continued)

FOREIGN PATENT DOCUMENTS

WO WO 2009/117646 A2 * 9/2009
WO WO2009117646 A2 9/2009

OTHER PUBLICATIONS

Chieu D. Tran, "Subnanogram Detection of Dyes on Filter Paper by Surface-Enhanced Raman Scattering Spectrometry", Anal. Chem. 56, 824-826 (1984).
J. P. Davies, S. J. Pachuta, R. G. Cooks, and M. J. Weaver "Surface-Enhanced Raman Scattering from Sputter-Deposited Silver Surfaces", Analytical Chemistry 1986 58 (7), 1290-1294.

(Continued)

*Primary Examiner* — Abdullahi Nur
(74) *Attorney, Agent, or Firm* — Mendelsohn Dunleavy, P.C.

(57) ABSTRACT

A method for the formation of flexible surface enhanced Raman spectroscopy substrates with filtering capabilities. The method produces thin flexible substrates that have a nanoparticle ink deposited thereon. The nanoparticle ink may be any suitable nanoparticle ink which includes stabilized nanoparticles such as silver, gold or copper nanoparticles. The substrates and nanoparticle ink undergo a thermal treatment for an amount of time sufficient to remove liquid vehicle and a substantial portion of the stabilizer. The thermal treatment provides a fractal aggregate nanoparticle layer on the substrate suitable for Raman spectroscopy. Such flexible SERS substrates may be used to detect trace amounts of analyte in large volume samples.

12 Claims, 13 Drawing Sheets

Related U.S. Application Data

(60) Provisional application No. 61/490,838, filed on May 27, 2011.

(51) Int. Cl.
  B82Y 20/00 (2011.01)
  B05D 5/06 (2006.01)

(56) References Cited

U.S. PATENT DOCUMENTS

| | | | |
|---|---|---|---|
| 7,563,324 | B1 | 7/2009 | Chen et al. |
| 2003/0059820 | A1 | 3/2003 | Vo-Dinh |
| 2004/0135997 | A1* | 7/2004 | Chan ............... C12Q 1/6825 356/301 |
| 2006/0060885 | A1 | 3/2006 | Wu et al. |
| 2007/0259437 | A1 | 11/2007 | Natan et al. |
| 2008/0276582 | A1* | 11/2008 | Boehrs ............... B01D 46/526 55/497 |
| 2011/0026019 | A1 | 2/2011 | Tyagi et al. |
| 2011/0037976 | A1 | 2/2011 | Zhao et al. |
| 2012/0058697 | A1* | 3/2012 | Strickland ............ B82Y 15/00 442/59 |

OTHER PUBLICATIONS

J.J. Lasema, A.D. Campiglia, and J.D. Winefordner; "Surface-Enhanced Raman Spectrometry on a Silver-Coated Filter Paper Substrate", Department of Chemistry, Analytica Chimica Acta, 208 (1988) 21-30, Elsevier Science Publishers B.V.

Y. Lu, G.L. Liu, L.P. Lee, "High-Density Silver Nanoparticle Film with Temperature-Controllable Interparticle Spacing for a Tunable Surface Enhanced Raman Scattering Substrate", 2004; American Chemical Society; NANO Letters; vol. 5, No. 1; pp. 5-9.

K.R. Wigginton and P.J. Vikesland, "Gold-Coated Polycarbonate Membrane Filter for Pathogen Concentration and SERS-based Detection", Analyst, 2010,135, 1320-1326.

L. Sona, J. Heathcote, A. Sklyarov, R. Klaper, V. V. Yakovlev, "Novel Approach for in Situ Biohazard Detection Utilizing Surface Enhanced Raman Spectroscopy", Proc. SPIE 5692, Advanced Biomedical and Clinical Diagnostic Systems III, 351-358 (Apr. 11, 2005).

M. Figueroa, W. Stephenson, K. Pourrezaei, S. Tyagi, "Characterization of Surface Enhanced Raman Scattering (SERS) Substrates Fabricated From Colloidal Printing Inks", Proc. SPIE 7576, Reporters, Markers, Dyes, Nanoparticles, and Molecular Probes for Biomedical Applications II, 75761T (Feb. 16, 2010).

\* cited by examiner

FLEXIBLE SERS SUBSTRATES WITH FILTERING CAPABILITIES

RELATED APPLICATION DATA

This application is a divisional of U.S. patent application Ser. No. 13/480,778, filed May 25, 2012, which claims priority to U.S. Provisional Application No. 61/490,838, filed May 27, 2011, the entire disclosure of which is hereby incorporated by reference as if set forth fully herein.

BACKGROUND OF THE INVENTION

1. Field of the Invention

The present invention is directed to forming surface-enhanced Raman spectroscopy (SERS) substrates. In particular, it is directed to flexible SERS substrates with filtering capabilities formed by using nanoparticle-based inks.

2. Description of the Related Technology

Raman spectroscopy (RS) is the measurement of the wavelength and intensity of light scattered inelastically from a molecule. FIG. 1 represents a schematic of the Raman spectrum. Raman scattering is the result of an inelastic collision of a photon with molecules. Both elastic and inelastic collisions occur when light interacts with a molecule. In elastic collisions (Rayleigh scattering), an atom is excited from a ground state to a higher energy state and then relaxes back to the original ground state, thereby emitting a photon at the same frequency as the incident light. However in an inelastic collision, the excited molecule relaxes to a different vibrational state rather than the original state, thereby scattering energy different from that of the incident light. If the scattered energy is higher than the energy of the incident light it is called an Anti-Stokes line (blue shifted), if it is lower it is called a Stokes line (red shifted).

RS gives information about the characteristic vibrational states of molecules. It is a widely used spectroscopic tool for the determination of molecular structure and for compound identification. The Raman scattering signals from the vibrational states of molecules are relatively weak. In order to obtain a satisfactory signal-to-noise ratio, one has to either increase the intensity of the probing laser or resort to surface enhanced Raman spectroscopy. For biological applications, increased laser intensity often limits the in vivo imaging capability of a system. In addition, RS has a small scattering cross section of about $10^{-30}$ $cm^2$ per molecule as compared to $10^{-16}$ $cm^2$ for fluorescence spectroscopy, thus reducing the possibility of analyzing compounds of biological significance due to the generally low concentration of analytes in biological samples. It is therefore desirable to create SERS structures that permit enhancement of Raman scattering signals for detection of biomolecules.

One such structure employs fractal aggregates of metallic colloidal particles formed on the surface of SERS substrates, typically constructed of Ag, Au, and Cu. Metallic fractal aggregates can exhibit some of the highest SERS signal amplification factors. A fractal is a self-similar geometrical object, i.e. it looks the same at any length scale. Fractal aggregates of metallic colloidal particles can enhance various linear and nonlinear optical responses, including Raman scattering. The basic mechanism that gives rise to such enhancement arises from the localization of optical plasmon excitations within small parts ("hot-spots") of a fractal aggregate. Such "hot spots" are usually much smaller (tens of nm) than the size of the fractal and often much smaller than the wavelength of the incident light used for detection. Fractal structures, unlike translationally invariant media, cannot support propagating waves and hence can confine electromagnetic fields to very small regions of the substrate. If sufficiently concentrated, the enhanced electromagnetic fields in the hot spots can result in SERS signal amplification.

The regions where the optical excitations are localized have very different local structures and, therefore, are characterized by different resonant frequencies. These nanoscale regions act as a collection of different optical "nanoresonators" resulting in a distribution of resonance frequencies in the visible and infra red spectral ranges and can have resonance quality-factors as large as $10^3$. When Stokes shifts are small, the SERS signal is roughly proportional to the local field raised to the fourth power and, therefore, it can be enhanced up to $10^{12}$ in the fractal hot spots.

When two nanoparticles come in close proximity without touching each other, the largest SERS signal amplification is achieved when the analyte molecule is sandwiched between two nanoparticles and when the polarization vector, i.e. the direction of the oscillating E-field of the laser's electromagnetic field, is along the line connecting the centers of the Ag nanoparticles. Amplification factors in the range of $6\times10^6$ to $2.5\times10^{10}$ have been predicted when the separation between two Ag nanoparticles of diameter 90 nm is varied between 5.5 and 1.0 nm. When the polarization vector is perpendicular to the Ag nanoparticles, the maximum amplification factor is relatively small (about 1 to 10). In FIG. 2 the polarization vector with respect to the molecules is shown. The amplification factor for the geometry indicated in [c] is intermediate between cases [a] and [b].

Certain methods of fabricating SERS substrates result in the noble metal nanostructures stochastically distributed over the substrate surface, e.g. electrochemically roughened electrodes, sputtered films, chemically etched films, electroless deposited films, and colloidal metal particles. An exemplary method incubates analyte in an Ag colloidal suspension (in water or other suitable liquid organic carrier) with 1.0-10.0 mM NaCl solution. The role of NaCl is as an aggregating agent. The Ag aggregates are then sorted according to their size and compact aggregates (two to about ten particles each) are isolated for further study using SERS. There are two drawbacks to this technique. First, there is no control over the size of the aggregates produced. The creation of hot spots for Raman scattering largely results as accidental byproducts of the technique. Thus, the reproducibility of SERS substrates made by this method is low. Second, the yield of the desired aggregates is very low and the suitable portions of the nanoparticle array on the substrate must then be selected from a mixture of larger aggregates before they can be used for SERS study. This hinders the fabrication of suitable SERS substrates on a large scale using this method.

Laserna et al. "Surface-enhanced Raman spectrometry on a silver-coated filter paper substrate," *Analytica Chimica Acta*, 1988, Vol. 208, pages 21-30, discloses a silver-coated filter paper as a SERS substrate. The filter paper has silver colloidal particles loosely attached to it. The lack of sufficient adhesion to the substrate by the particles causes quick deterioration of the amplification factor over time. In addition, the inter particle spacing is not controlled, but instead is the result of a stochastic process. A similar disclosure is also found in, "Subnanogram Detection of Dyes on Filter Paper by Surface-Enhanced Raman Scattering Spectrometry," Chieu D., Tran, *Anal. Chem.*, 1984, 56, pp. 824-826.

Another method for fabrication of SERS substrates employs controlled patterning of the nanostructures with electron-beam lithography. One advantage of this method is that little randomness remains and one can expect the SERS signal to be homogeneous across the proposed substrate. Such substrates are now commercially available (Mesophotonics Limited, Southampton, UK). Fabrication of such substrates involves a multi-step process and the resulting substrates are quite expensive. Such substrates are also small in size, for example, typically on the order of 4 mm×4 mm.

Sona et al. "Novel approach for in situ biohazard detection utilizing surface enhanced Raman spectroscopy," *Proc. Of SPIE,* 2005, Vol. 5692, pages 351-358, teaches an SERS material made from silver vacuum-evaporated on a fiberglass porous membrane having pore sizes on the order of 1 micron, as well as a chemically deposited thin silver layer on a glass fiber filter. This SERS material was demonstrated for detection of low concentrations of clofibric acid in a liquid and showed the ability to detect the analyte at an extremely low detection level.

U.S. Patent Application publication no. 2007/0259437, discloses nanoparticles coated with a filtering film, which is made from a permselective organic coating agent. The filtering film traps a variety of molecules, but allows the analyte of interest to selectively pass through the film to reach the nanoparticles. RS can then detect the analyte.

U.S. Patent Application publication no. 2006/0060885 discloses a method for depositing a conductive nanoparticle layer onto a substrate surface. A solution of stabilized nanoparticles is applied to a substrate surface and heated to remove liquid vehicle and stabilizer. Heating causes the metal nanoparticles to coalesce to form an electrically conductive layer. Heating is continued until a minimum conductivity of 1 Siemens/centimeter is achieved in order to provide the conductive coating.

The current commercially available SERS substrates have three serious limitations: (a) reproducibility, (b) cost-effectiveness and (c) a small active area (typically 4 mm×4 mm) and the constraint that the analyte has to be brought into intimate contact with the substrate. These limitations make the commercial SERS substrates impractical for detecting molecules of interest in trace amounts or which are dispersed over a large area, e.g. a bio-toxic aerosol released in a large room or a trace amount of bio-hazardous substance released in large volumes of water. In principle it is possible to filter out the molecule(s) of interest and then transfer them to a SERS substrate for further analyses. In practice this is very cumbersome for dilute specimens and therefore is rarely used. The ability to sense molecules of interest at low concentrations is especially critical for effective response to an industrial accident or an act of terrorism or to enhance security at places that may be susceptible to acts of terrorism.

Therefore, there is a need to provide a method for forming SERS substrates that permits control of the average distance between nanoparticles and which provides SES substrates suitable for use to detect trace amounts of analytes in samples of large volumes.

SUMMARY OF THE INVENTION

An object of the invention is to provide a method for producing flexible SERS substrates that have filtering capabilities.

Yet another object of the invention is to provide a method for controlling the average distance between nanoparticles on a flexible SERS substrate.

An aspect of the invention may be a method for fabricating SERS substrates comprising the steps of: providing a porous flexible substrate; applying a nanoparticle ink to a surface of the porous substrate, wherein the nanoparticle ink comprises a liquid and a plurality of nanoparticles; and heating the nanoparticle ink and the porous substrate for a period of time, whereby a SERS substrate is formed.

Yet another aspect of the invention can be a flexible SERS substrate comprising: a porous substrate and a fractal aggregate of a plurality of nanoparticles attached to the substrate.

One more aspect of the invention can be a method for using flexible SERS substrates with filtering capabilities to detect trace amounts of analyte molecules in a large volume sample comprising the steps of: filtering a sample through an SERS substrate and using RS to detect an analyte on the SERS substrate.

DETAILED DESCRIPTION OF THE PREFERRED EMBODIMENT(S)

The present invention produces a flexible SERS substrate with filtering capabilities that can directly filter low concentration analyte molecules present in large volume samples and then detect the analyte using RS. The flexible SERS substrates have a wide distribution of nanoparticle cluster sizes and interparticle distances that can be fractal-like. The present fabrication method for SERS substrates may provide a finer control over the inter-particle separations and the nanoparticle cluster sizes than conventional fabrication methods; may robustly attach the nanoparticles to the underlying substrate minimizing their movement under laser irradiation, and may create a truly three-dimensional substrate that allows analyte molecules to anchor at multiple sites. This results in confinement of the electromagnetic field. Also, the formed nano-cavities provide further amplification due to their high quality factors.

These three features of the present fabrication technique allow the production of SERS substrates with reproducible ultra-high amplification factors that are three to four orders of magnitude better than the best commercially available SERS substrates. The SERS substrates of the invention can also be considerably less expensive than commercially available SERS substrates.

The SERS substrates of the present invention have a filtering capability which enables them to be used to rapidly detect trace amounts of analytes such as biological threat agents in large volumes of air, water, bio-fluids or exhaled breath in real time. This will offer the ability to enhance the effectiveness of a response to an industrial accident or an act of terrorism or to enhance security at places that may be susceptible to acts of terrorism.

Figure 4:
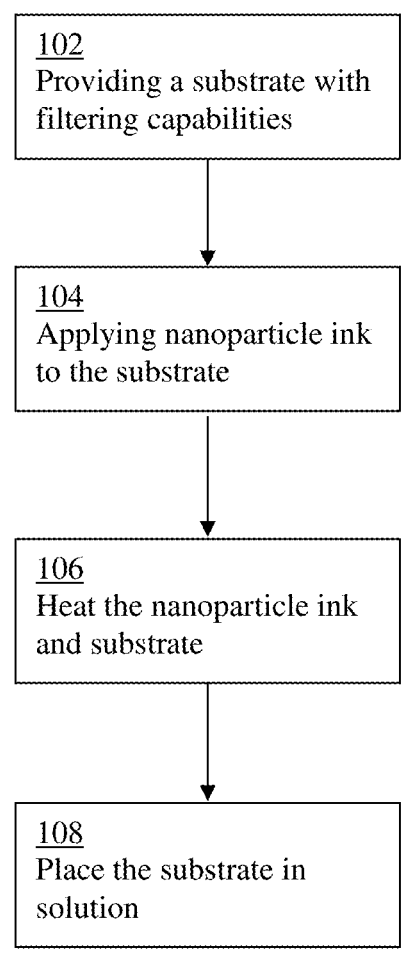
FIG. 4 is flow chart of a method for forming a flexible SERS substrate with filtering capabilities in accordance with an embodiment of the present invention.

FIG. 4 illustrates a process for forming a flexible SERS substrate. In step 102 one or more flexible substrates 10 with filtering capabilities are provided. Suitable substrates 10 may be any substrate that is flexible, porous, and able to withstand moderate temperatures. Suitable substrates may be fabric-based substrates made from natural or man-made fibers, such as fiberglass, cellulose fibers and polyimide fibers. The substrate can be metallic or non-metallic and can be woven, spun or made by any other suitable fabrication method. The porosity of the filter substrate will be dependent on the size and nature of the analyte to be separated or agglomerated by the filtering action of the SERS substrate.

In step 104, nanoparticle ink 20 is attached to substrate 10. Nanoparticle ink 20 may be air-brushed onto the heated quartz substrate 10. Alternatively, Ag colloid films (made from inks that are 25-40% by weight Ag) can be deposited on polyimide substrates.

Figure 1:
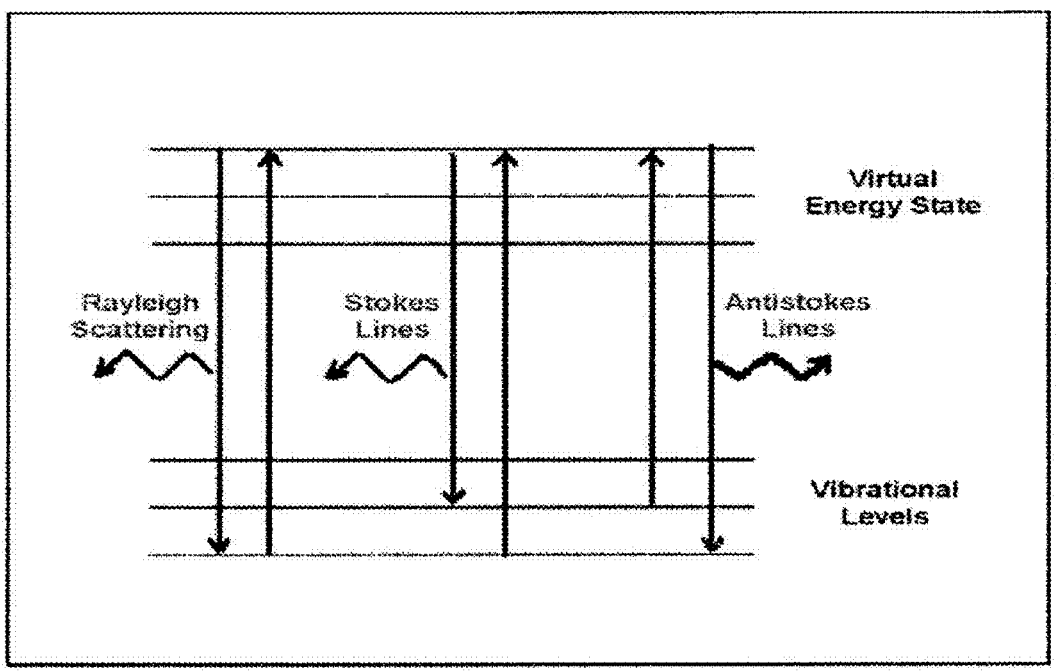
FIG. 1 is a diagram illustrating the elastic (Rayleigh) and inelastic (Raman) scattering of photons by a molecule.
Figure 2:
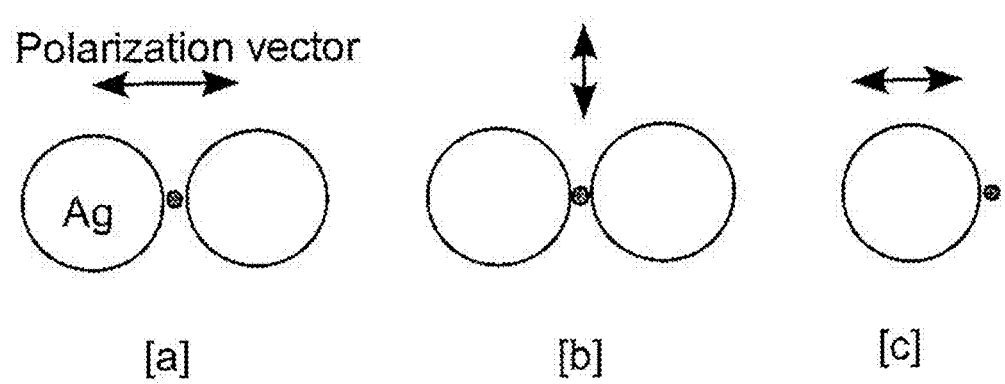
FIG. 2 shows the polarization vector with respect to molecules.
Figure 3A:
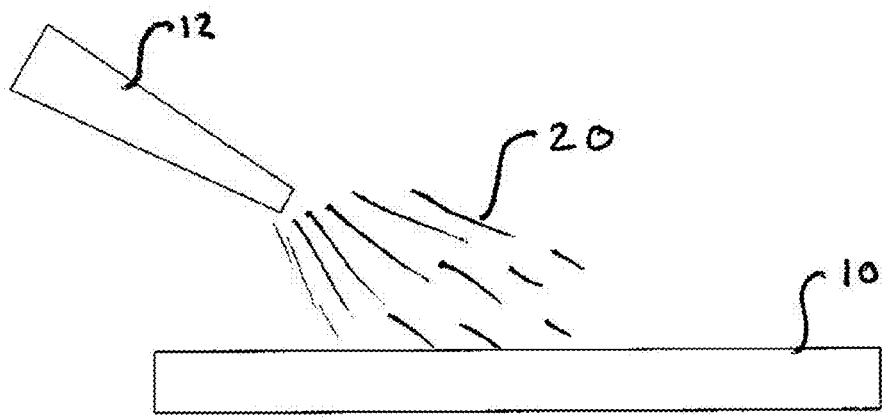
FIG. 3(a) shows an applicator and a substrate in accordance with an embodiment of the present invention.

FIG. 3(a) illustrates the application of nanoparticle ink 20 onto a substrate 10. The nanoparticle ink 20 may be applied in a variety of ways. It should be understood that the method of applying nanoparticle ink 20 to substrate 10 may include any method that will form a suitable thin coating on substrate 10. Processes for attaching nanoparticle ink 20 to substrate 10 include, for example, airbrushing, ink jet printing, silk screen printing, stamping (such as microcontact printing), gravure printing methods, flexographic printing, stencil printing and the like. The deposited ink 20 may have a thickness ranging from about 5 nm to about 1 millimeter, particularly from about 10 nm to 1 micrometer. The filters may also be coated by dipping them directly in the nanoparticle inks.

Figure 3B:
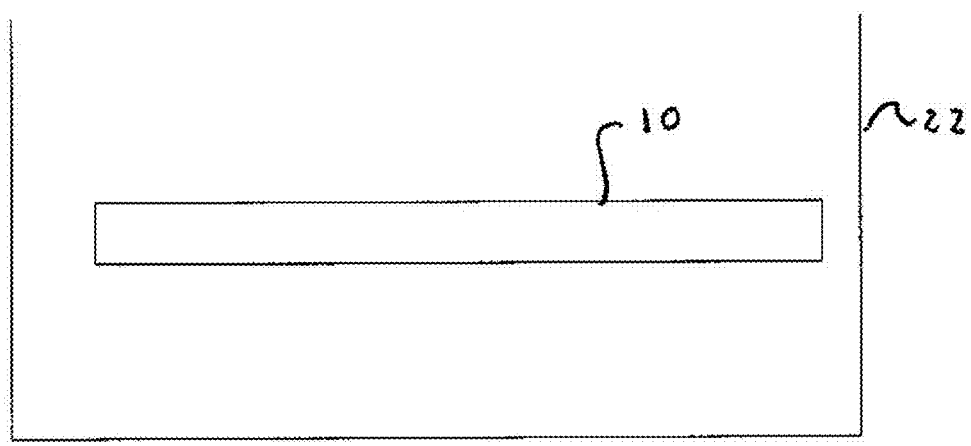
FIG. 3(b) shows a substrate and an oven in accordance with an embodiment of the present invention.

Still referring to FIG. 4, in step 106, substrate 10 and nanoparticle ink 20 may be heated to a suitable temperature, preferably, between about 100-250° C., more preferably, between about 150-200° C., in, for example, oven 22. Preferred temperature ranges are dictated by the sintering characteristics of the nanoparticle inks. For some silver inks the sintering can take place at 50-60° C. whereas for some gold inks the temperatures can be as high as 300-350° C. FIG. 3(b) shows a substrate and an oven in accordance with an embodiment of the present invention. The duration of heating may be sufficient for removal of liquid vehicle, and a portion or all of other additives that may be present in the nanoparticle ink 20, such as the adhesion promoters, rheology modifiers, surfactants and some or all of stabilizer 17. The typical heating duration may be between 5-30 minutes. Preferred time ranges are dependent on the annealing temperatures. Shorter times are required for higher annealing temperatures. However, shorter annealing times are more susceptible to small variations in experimental variables. At longer annealing times at lower temperatures, the process can withstand small variations in temperature and time of annealing and still yield reproducible results. Annealing times of 10-20 minutes are often suitable. Heating may also be achieved by such means as microwaves and laser heating.

In step 106, at least a portion of stabilizer 17 is controllably removed by heating. In some embodiments, heating may decompose a portion of the stabilizer to produce "decomposed stabilizer," which may also be removed by heating such that both stabilizer 17 and decomposed stabilizer generally are not incorporated into the nanoparticle layer, but if present are in a residual amount. Separation of the stabilizer 17, the liquid, and the decomposed stabilizer from the metal nanoparticles 18 may occur in any manner such as for example a change in state of matter from a solid or liquid to a gas, e.g., volatilization. Separation may also occur when any one or more of the stabilizer, decomposed stabilizer, and liquid migrates to an adjacent layer and/or forms an interlayer between the nanoparticle layer and the adjacent layer, where intermixing of various materials optionally occurs in the adjacent layer and/or the interlayer.

In embodiments, a residual amount of one or more of the stabilizer, decomposed stabilizer, and the liquid may be present in the nanoparticle layer, where the residual amount does not appreciably affect the Raman scattering of the nanoparticle layer, or the resulting Raman scattering is still within the useful range for the intended device. The residual amount of each component may independently range for example of up to about 5% by weight, or less than about 0.5% by weight based on the weight of the nanoparticle layer. In addition, the residual amount of stabilizer shell leaves a fine coating between the nanoparticles and the supporting substrate. This provides an adhesive anchoring of the nanoparticle to the substrate that makes the flexible SERS substrates more enduring overtime.

When separation of the stabilizer 17 and/or decomposed stabilizer from the metal nanoparticles occurs, the attractive force between the separated stabilizer/decomposed stabilizer and the metal nanoparticles 18 is severed or diminished, which cause nanoparticles 18 to form a fractal aggregate. Other techniques such as exposure to UV light may be combined with heating to accelerate the separation of the stabilizer, the liquid, and the decomposed stabilizer from the metal nanoparticles 18.

The length and duration of heating controls the removal of stabilizer 17, which in turn affects the distance between nanoparticles 18. The layer of nanoparticles preferably includes a number of spaces 19, as shown in the FIGS. 5(a)-5(b). The temperature and duration of heating can be adjusted to control the average distance between nanoparticles 18. The average distance between nanoparticles 18 is typically defined over the cross-sectional area of the laser beam used in the Raman scattering. The inter-nanoparticle distance is the most important parameter that determines the SERS substrate amplification.

Heating also enhances the adhesion of the nanoparticles to the substrate. This is due to the fact that some of the stabilizer remains in the SERS substrate after heating which may provide a thin coating between the substrate and the nanoparticles which enhances adhesion of the nanoparticles to the substrate. This effect is important since it reduces the substrate aging which is a significant problem in some prior art SERS substrates.

It should be understood that the creation of nanoparticles or nanoparticle clusters located in close proximity to one another with a distribution of different spacing 19, is desired. The different distances between nanoparticle clusters provide a variety of "hot-spots" suitable for different lasers in the same SERS substrate. This allows a single substrate to be used with a variety of different lasers, eliminating the need to customize SERS substrates for particular lasers.

Figure 5A:
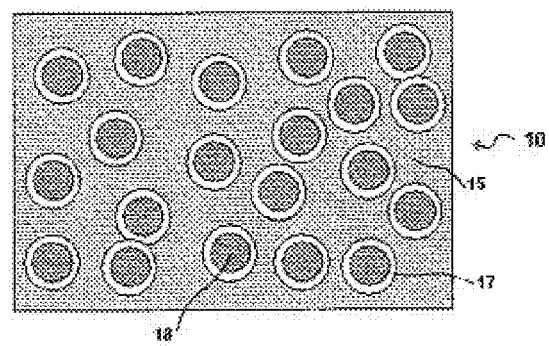
FIGS. 5(a)-5(b) schematically illustrate the effects of heat treatment on the nanoparticle ink.
Figure 5B:
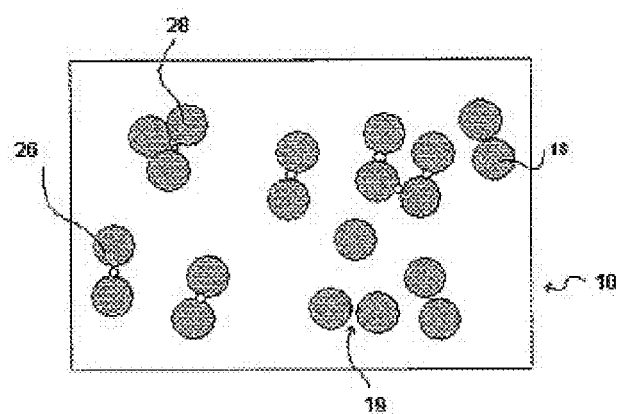

The effects of step 106 on the nanoparticle layer are schematically depicted in FIGS. 5(a)-5(b). FIG. 5(a) shows the components of nanoparticle ink 20 when it is initially attached to substrate 10. Shown are nanoparticles 18, liquid vehicle 15 and stabilizer 17. FIG. 5(b) shows the substrate surface with fractal aggregates of nanoparticles after removal of liquid vehicle 15 and stabilizer 17. In a fractal aggregate, the distances between different sets of particles 18 form a range. As shown in FIG. 5(b), some of the resultant materials are spaced apart as indicated by 19, while some of the nanoparticles may be touching, bound or held together to form larger agglomerated particles 26 and 28.

The method of the present invention is highly reproducible, typically showing maximum variations in the amplification factor of about 10% from substrate to substrate. The fibers that constitute the glass fiber substrate provide a three dimensional skeleton which supports the metallic nanoparticles. The randomness of the underlying fibrous structure combined with a wide distribution in the cluster sizes of the metallic nanoparticles averages out the local topographical variations and the resulting SERS amplification factors at the submicron level when interrogated with laser beam dimensions of about 10-50 µm. Unlike planar substrates, the three-dimensional nature of the present filter substrates provides multiple anchoring sites for an analyte molecule. This multiple anchoring further contributes to SERS signal amplification.

Figure 6A:
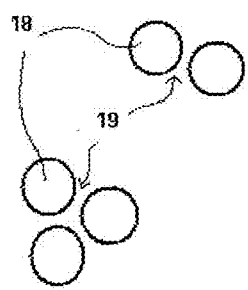
FIGS. 6(a)-6(c) show the potential arrangements of various nanoparticles during the formation of an SERS substrate.
Figure 6B:
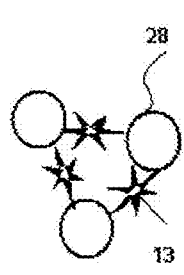
Figure 6C:
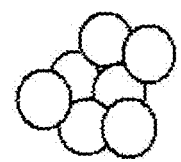

FIGS. 6(a)-6(c) show a variety of potential arrangements of nanoparticles 18 which may result from step 106. In the heating process, at least two nanoparticles 18 are brought into proximity with each other, i.e. a minimum distance between the nanoparticles 18 is maintained. In order to obtain the fractal aggregates, a significant number of the nanoparticles 18 or nanoparticle clusters must remain spaced apart from each other by a minimum distance on the order of a few nanometers, such as shown in FIG. 6(a). Also, to render the SERS substrate suitable for use with a variety of different lasers, the minimum distance between pairs of nanoparticles 18 or nanoparticle clusters varies from location to location. In other words, certain nanoparticles 18 or nanoparticle aggregates do not touch or sinter, instead forming a bond 13, such as shown in FIG. 6(b). The spacing 19 between nanoparticles or nanoparticle aggregates provides the SERS amplification and forms "hot-spots." The number of spaces between particles that may exist on a SERS Substrate 10 will be diminished as an increasing number of interconnected clusters such as those shown in FIG. 6(c) are formed The temperature and duration of step 106 can be adjusted to control the average distance between nanoparticles 18. Several different methods can be used to determine the average distance between nanoparticles 18 during the fabrication process. Thus, a skilled person may use one of these methods to determine the optimal temperature and duration for heat treatment step 106, in order to manufacture the SERS substrates with the desired inter-particle distances.

Figure 7:
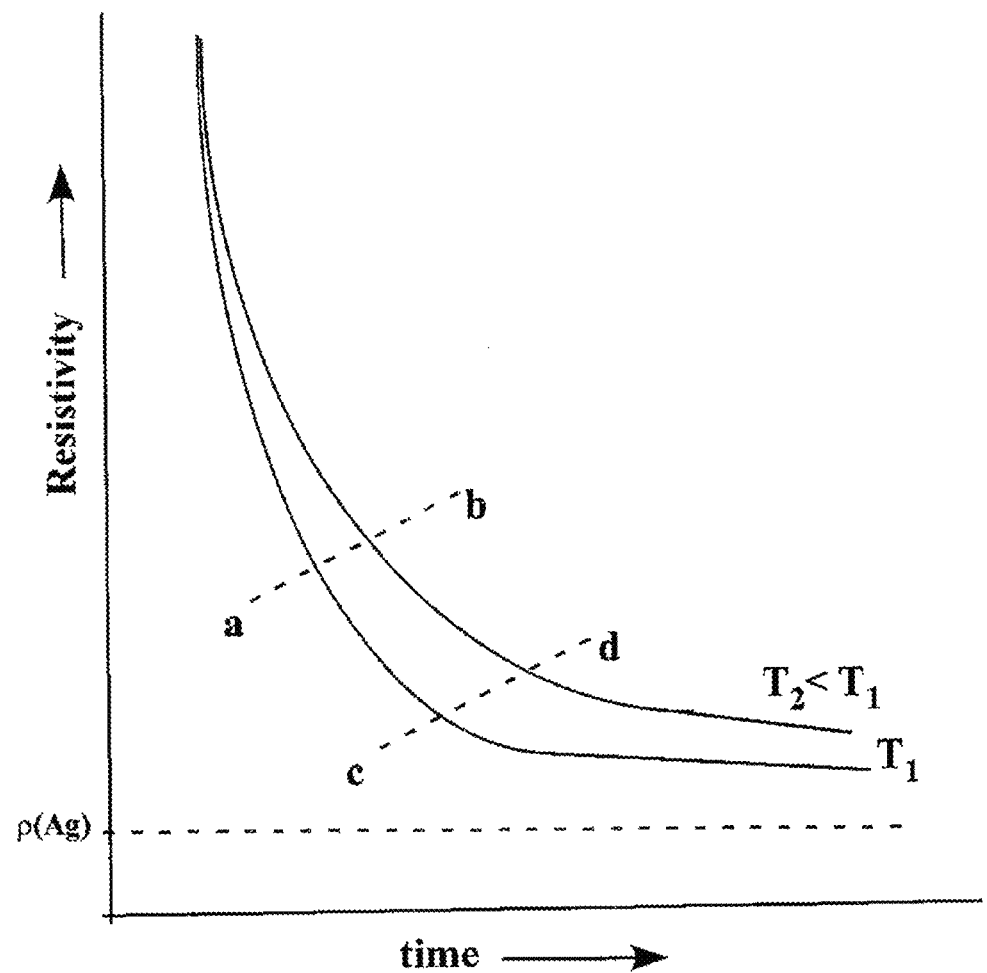
FIG. 7 is a graph of resistivity vs. time (t).

One method for determining interparticle distance is by monitoring the resistivity of the substrate, as detailed in Jean-Francois Gouyet, *Physics and Fractal Structure*, Springer, Berlin, 1996, Chapter 3. FIG. 7 is a graph of resistivity as a function of time of heating at two different temperatures $T_1$ and $T_2$ for silver colloidal films. Typically, the heating temperature is in the range of 100-250° C. for silver colloidal films. At t=0 these films have such high resistance that they are close to being electrical insulators for direct current conduction. This is due to the substantially complete isolation of nanoparticles 18 from each other. As stabilizer 17 is removed, the nanoparticles 18 begin to move closer together and, in some cases, make isolated connections and the resistivity shows a decline. With prolonged time of annealing, typically 5 to 30 minutes (with shorter times at higher heating temperatures), the resistivity can be lowered to within an order of magnitude of bulk silver which is $1.62 \times 10^{-8}$ Ω·m (1.62 µΩ·cm). Typically, suitable SERS substrates have a conductivity of from about 2000 to about 5000 S/cm or a resistivity of from about 2.0 to $5.0 \times 10^{-4}$ Ω·cm. The desired resistivity for SERS substrate 10 is a resistivity that corresponds to the situation where nanoparticles 18 are not densely networked but are also not completely electrically isolated from each other. This happens in a region bound by, for example, the lines a-b and c-d of FIG. 7.

Figure 8:
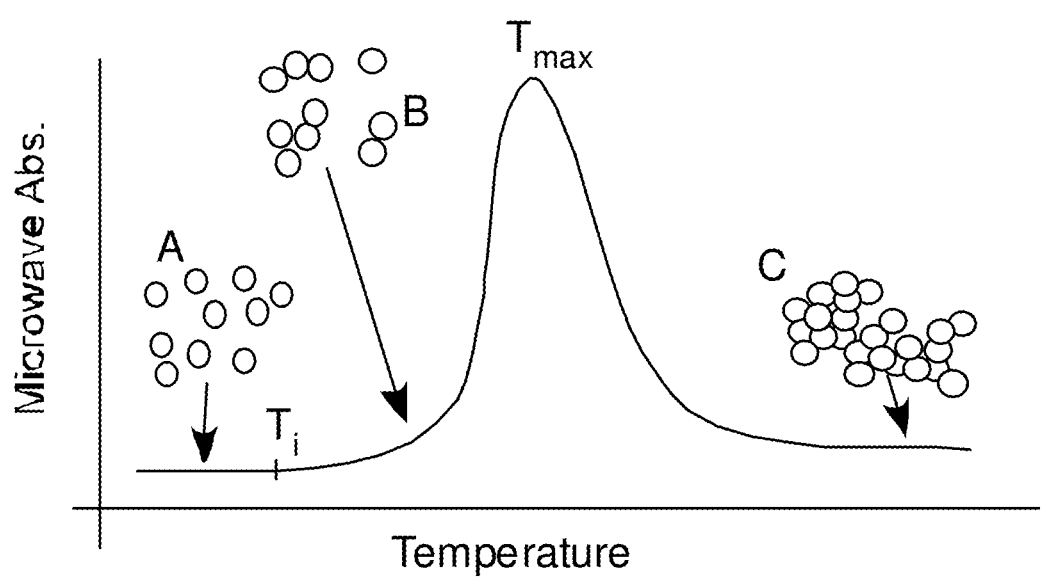
FIG. 8 shows microwave absorption in relation to the temperature of heat treatment.

Another method of determining the optimal temperature and duration of step 106 is by monitoring microwave absorption of the substrate, as show in FIG. 8. In one embodiment, the heating process is optimized by monitoring microwave (~10 GHz) absorption by the Ag nanoparticles. FIG. 8 shows absorption of microwave at frequency of about 10 GHz as the substrate is heated at approximately 6° C./min. At low temperature, $T_t$, the nanoparticles are not aggregated (A) and microwave absorption is minimal. As the temperature is increased, the microwave absorption increases as polymer shells surrounding the particles are removed and nanoparticles begin to get closer together (B). The microwave absorption will reach a maximum and then decrease as sintering increases, which also results in larger nanoparticle clusters (C). The most promising heating temperature region is found near where the microwave absorption first begins to rise steeply. In this temperature region, the inter-particle distance can be adjusted by varying the heating time. Suitable nanoparticle spacing is achieved by identifying when sintering begins and controlling the duration of sintering as determined by the microwave monitor.

A further method of determining the optimal temperature and duration of step 106 may be monitoring the SERS amplification factor as a function of temperature and duration of heat treatment. Since the SERS amplification factor depends very sensitively on the inter-particle separation, the SERS amplification factor is an indirect index of the inter-particle distance. So one may measure the amplification factor of the SERS substrate to achieve the desired average distance between nanoparticles. For example, the heating process 106 of the present invention should typically be terminated when an amplification of the Raman scattering signal of from about $1 \times 10^3$ to about $2.5 \times 10^{10}$, more preferably, from about $1 \times 10^6$ to about $1 \times 10^9$ and most preferably from about $1 \times 10^7$ to $6 \times 10^8$, is achieved. Amplification is determined using a normal Raman substrate which has not been provided with a Raman signal enhancing component, e.g. a glass slide without a coating can be used as a normal Raman substrate.

Typically, the spacing between certain pairs of nanoparticles and/or nanoparticle clusters in the SERS substrate should be in the range of from about 0.1 to about 10 nm, more preferably from about 0.5 to about 8 nm and, most preferably, from about 1.0 nm to about 5.5 nm in order to create the desired hot spots.

In the embodiment discussed herein, a silver (Ag) nanoparticle ink 20 is used. Nanoparticle ink 20 may have nanoparticles 18 that are between 15-50 nm in diameter and comprise up to 1% by weight of the total weight of the nanoparticle ink located within a liquid vehicle 15. However it should be understood that the process is not limited to the use of silver nanoparticle ink 20, but can be applied to other conductive nanoparticle inks 20, such as Au and Cu.

The nanoparticle ink 20 also includes a liquid vehicle 15 which may optionally include an adhesion promoter, surfactants and/or rheology modifiers; and a stabilizer 17, which acts as an agglomeration preventer and/or rheology modifier.

A suitable liquid vehicle 15 for nanoparticle ink 20 may be selected from, for example, water, ketones, alcohols, esters, ethers, halogenated aliphatic and aromatic hydrocarbons and the like and mixtures thereof. Specific examples of suitable liquid vehicles are cyclohexanone, acetone, methyl ethyl ketone, methanol, ethanol, butanol, amyl alcohol, butyl acetate, dibutyl ether, tetrahydrofuran, toluene, xylene, chlorobenzene, methylene chloride, trichloroethylene, and the like. A single material or a mixture of two, three or more different materials from the foregoing list can be used in any combination and at any suitable ratio such as an equal or unequal ratio of two or more different fluids.

Adhesion promoters may be materials such as polytetrafluoroethylene and metal complexes of Pd, Mg, W, Ni, Cr, Bi, B, Sn, In, Pt. The adhesion promoters permit nanoparticles 18 to remain attached to the surface of substrate 10, after the heating process.

The stabilizer 17 may be any moiety that "stabilizes" nanoparticles 18 prior to and/or during deposition of the nanoparticle ink 20, where "stabilizes" refers to reducing the aggregation and precipitation of nanoparticles 18. Preferred stabilizers 17 are those that "stabilize" metal nanoparticles 18 at room temperature, which refers herein to a temperature from about 20° C. to about 28° C., or any other desired temperature range. Stabilizer 17 may be a single stabilizer 17 or a mixture of two or more stabilizers 17. In some embodiments, stabilizer 17 may have a boiling point or decomposition temperature lower than about 250° C., particularly lower than about 150° C., under 1 atmosphere or a reduced pressure of, for example, from several mbar to about $10^{-3}$ mbar.

The stabilizer 17 may be a coating or partial coating material which may be made of a material such as PVP (polyvinylpyrrolidone), another polymer, or borohydride. Polymers that have been successfully used in the formulation of inks are Triton X-100, Triton X-15, Triton X-45, Triton QS-15, linear alkyl ether (colar Cap MA259, colar Cap MA1610), quaternized alkyl imidazoline (Cola Solv IES and Cola Solv TES), polyvinyl alcohol, polyethylene glycol, and polysiloxanes. The weight percentage of stabilizer 17 may vary from 0.5% to 20%. The loading of nanoparticles 18 may be from 10% to up 60%.

The rationale behind the use of polymers as stabilizers 17 is that they often have higher viscosities than do the typical liquids used as vehicles in conductive inks. Because of their multiple binding sites to metal nanoparticles, they can be used in lower concentrations than monomeric dispersants, and still confer monolayer coverage of the metal nanoparticle. Higher viscosities are important because they facilitate the creation of good dispersions of inks that can be printed using inkjet methods. Lower concentrations of the dispersant are favorable because there is less organic material to be removed during the curing process.

In some embodiments, stabilizer 17 may be an organic stabilizer. The term "organic" herein refers to the presence of carbon atom(s), but the organic stabilizer may include one or more non-metal heteroatoms such as nitrogen, oxygen, sulfur, silicon, a halogen, and the like. Exemplary organic stabilizers include for instance thiol and its derivatives, amine and its derivatives, carboxylic acid and its carboxylate derivatives, polyethylene glycols, and other organic surfactants. In some embodiments, the organic stabilizer is selected from the group consisting of a dithiol such as for example 1,2-ethanedithiol, 1,3-propanedithiol, and 1,4-butanedithiol; a diamine such as for example ethylenediamine, 1,3-diaminopropane, 1,4-diaminobutane; a thiol such as for example 1-butanethiol, 1-pentanethiol, 1-hexanethiol, 1-heptanethiol, 1-octanethiol, 1-dodecanethiol, and tert-dodecanethiol; an amine such as for example 1-ethylamine, 1-propylamine, 1-butylamine, octylamine and dodecylamine; a mixture of a thiol and a dithiol; and a mixture of an amine and a diamine, particularly a low boiling point version of any of the above. Organic stabilizers containing a pyridine derivative (e.g., dodecyl pyridine) and/or organophosphine that can stabilize metal nanoparticles are also included as a stabilizer in embodiments of the present invention. In some embodiments, metal nanoparticles 18 may form a chemical bond with stabilizer 17.

In some embodiments, stabilizer 17 may be a metal containing stabilizer such as organometallic compounds or metal salts of organic compounds. Illustrative examples are metal alkoxides, metal carboxylates, alkyl ammonium salts of metal, and other metal containing compounds such as a metal alkylsulfonate or arylsulfonate, and a pyridinium salt of metal, or mixtures thereof. The metal of the metal containing stabilizer can be for example sodium, potassium, and calcium. In some embodiments, the metal containing stabilizer is other than a metal-chelate complex. In some other embodiments, stabilizer 17 may be material other than a metal containing stabilizer.

The extent of coverage of stabilizer 17 on the surface of nanoparticles 18 can vary depending on the capability of stabilizer 17 to stabilize nanoparticles 18, for example from partial to full coverage. Of course, there may also be variability in the extent of coverage of stabilizer 17 among individual nanoparticles 18. Stabilizer 17 may function as a barrier layer which prevents contact between the surfaces of adjacent nanoparticles 18. Alternatively, stabilizer 17 may be in the form of a plurality of, for example, ligands bound to the surface of nanoparticles 18 which provide spacing between adjacent nanoparticles 18 via steric hindrance. Suitable stabilizers 17 must be capable of being partially or completely removed by heating substrate 10 and nanoparticles 18 at a temperature below which damage to substrate 10 or nanoparticles 18 would occur.

Exemplary amounts of the composition components in ink 20 are as follows. The metal nanoparticles 18 and the stabilizer 17 may be present in an amount ranging for example from about 0.3% to about 90% by weight, or from about 1% to about 70% by weight, the balance being the other components of the composition such as the liquid vehicle. If the metal nanoparticles 18 and the stabilizer(s) 17 are added separately into the liquid vehicle, the metal nanoparticles are present in an amount ranging, for example, from about 0.1% to 90% by weight, or from about 1% to 70% by weight of the composition. Stabilizer 17 is present in a sufficient amount to form a stable composition, for example in a range from about 1% to 50% by weight, or from about 5% to 40% by weight of the composition.

In addition to high SERS signal amplification, the flexible SERS substrate also has the advantage of being capable of detecting extremely low concentrations of analyte molecules in large volumes of material. The SERS substrates of the present invention can be incorporated into a portable Raman sensor device for rapidly detecting low concentrations of analytes of interest, such as biological threat agents.

Figure 10:
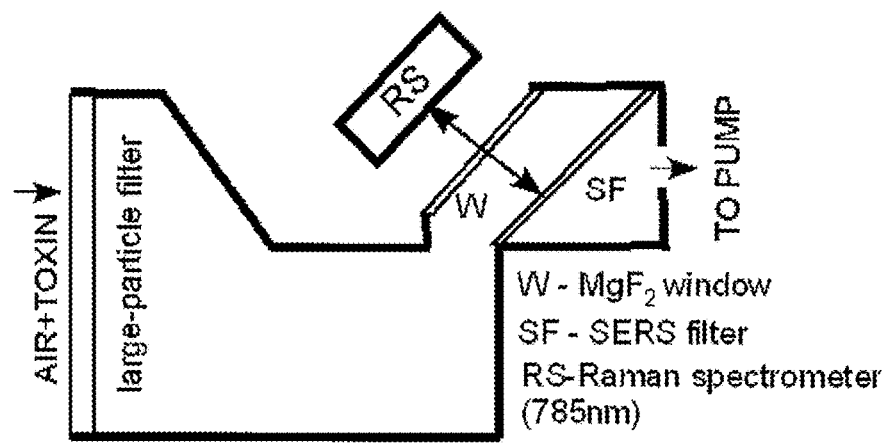
FIG. 10 illustrates a portable device which can be used to detect a trace amount of analyte in a large volume sample.

A suitable portable device is shown in FIG. 10 and may include the SERS substrate, a means for forcing sample through the SERS substrate, such as a pump, a sample inlet and a sample outlet. The portable device may also include a means for excitation of the SERS substrate, such as a laser or other suitable excitation device, and a means for determining the wavelength of radiation emitted from said SERS substrate responsive to excitation. Optionally, the portable device may include a means for correlating the determined wavelength of the emitted radiation with an analyte. Other optional features of the device may include a display means for displaying the determined wavelengths and/or a selection of analytes correlated to said wavelengths, a means for measuring the flow of sample through said SERS substrate, a means for determining an area of a signal for a particular analyte interest and a means for calculating a concentration of said analyte in the sample from the measured sample flow and area of the signal.

One more aspect of the invention can be a method for using flexible SERS substrates with filtering capabilities to detect trace amounts of analyte molecules in a large volume sample comprising the steps of: filtering a sample through an SERS substrate and using RS to detect an analyte on the SERS substrate. An exemplary portable device for implementing the SERS substrates of the invention is set forth in FIG. 10. The sample is forced through the flexible SERS substrate, while the substrate functions as a filter to trap the analyte molecules. The sample may be forced through the substrate using a pump or other suitable means. Optionally, the sample may be pre-filtered to remove large particles which are not of interest for detection.

The analyte molecules that are trapped on the substrate can be detected using RS. Specifically, the SERS substrate containing the trapped analyte is subjected to excitation energy, such as laser irradiation, and the nanoparticles emit light at a wavelength indicative of the analyte. In one example, a laser emitting light at a wavelength of 784 nm is used for Raman excitation. The predominant mechanism giving rise to high SERS amplification factors is the surface Plasmon resonance (SPR) induced in the nanoparticles. The SPR frequency depends on the size of the nanoparticle clusters, Due to a distribution in the size of the clusters SPR can be induced by a wide range of excitation wavelengths. Thus Raman excitation lasers can be of various wavelengths. Typically, a suitable wavelength range may be from 480 nm to 1000 nm.

The flexible SERS substrates of the present invention are able to detect analytes in sub-nanomolar concentrations in large volumes, which is 1000 to 10000 times better than commercially available SERS substrates.

In addition, the SERS substrates of the invention can be employed to determine the concentration of the analyte in the sample. This is accomplished by measuring the amount of sample passed through the SERS substrate for filtering, integrating the area under the peak at the wavelength of interest for the analyte and calculating the concentration of the analyte in the sample from this information.

Example 1

Figure 9A:
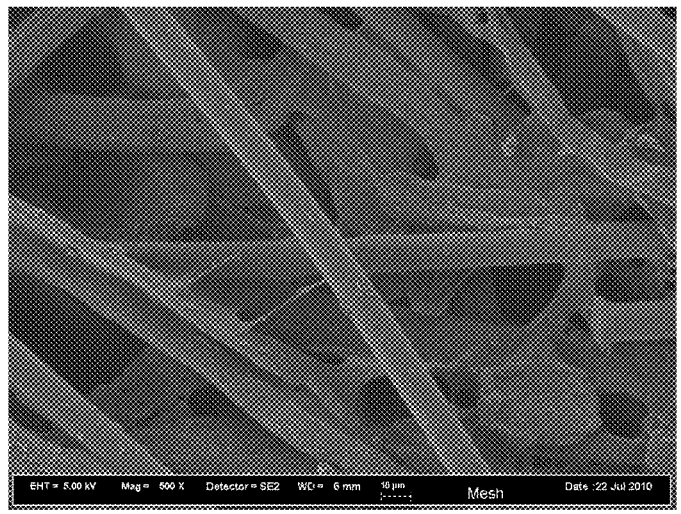
FIGS. 9(a)-9(c) are SEM micrographs showing the changes in a silver nanoparticle coated filter fiber as a result of heat treatment.
Figure 9B:
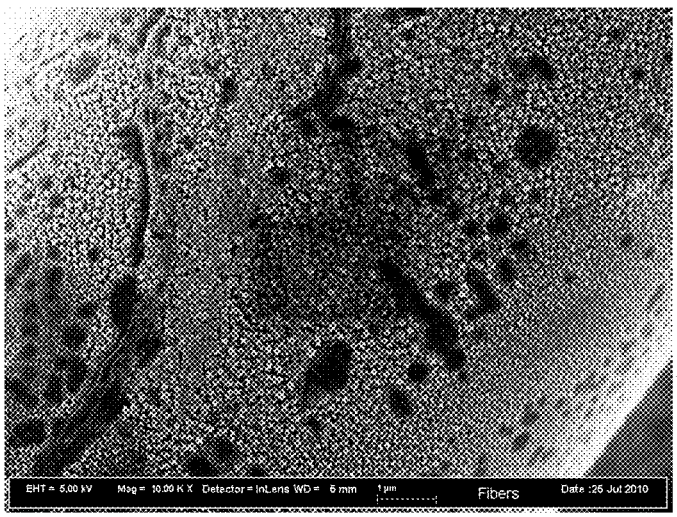
Figure 9C:
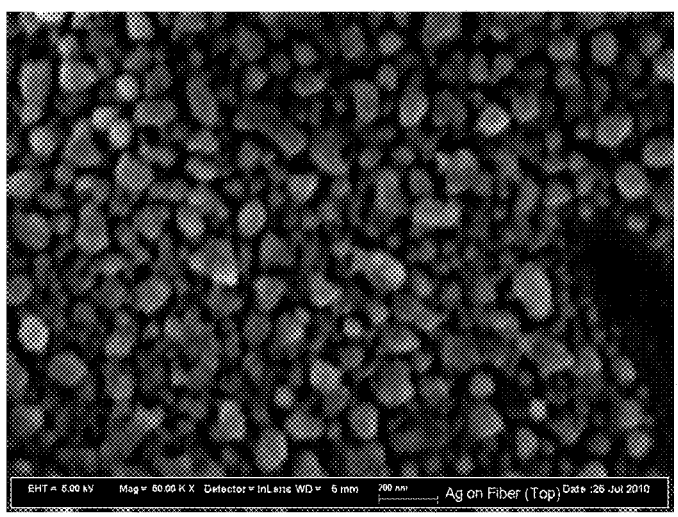
Figure 11:
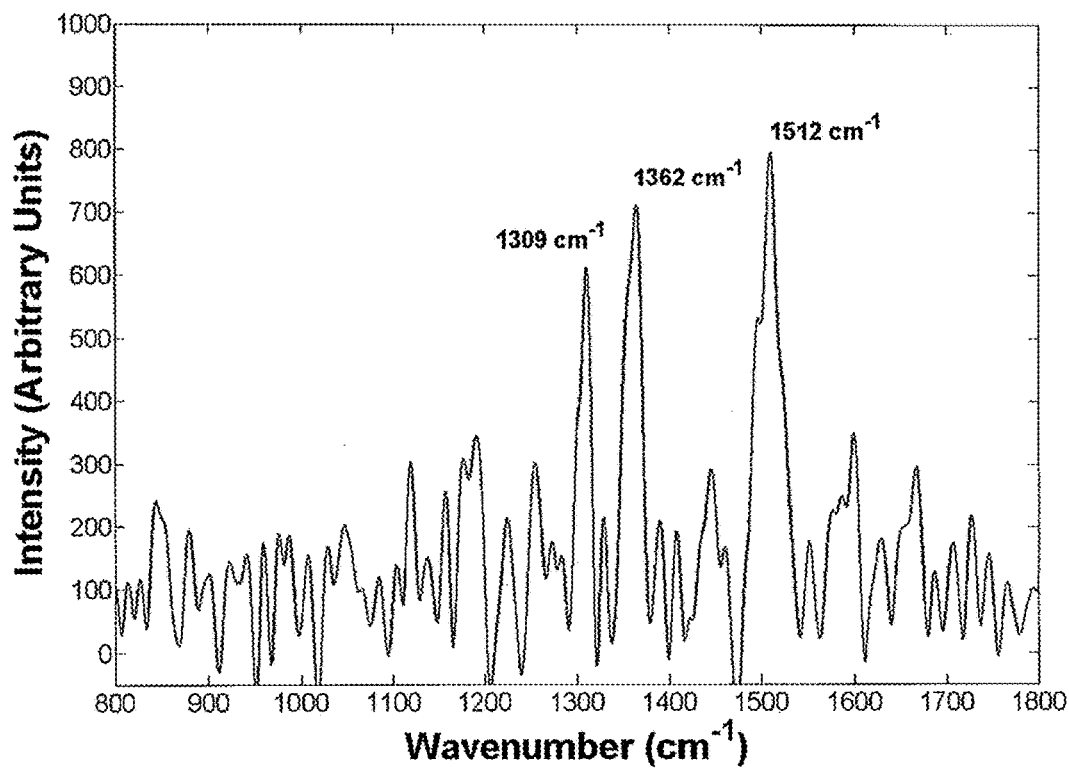
FIG. 11 is a graph showing the Raman scattering spectrum of Rhodamine on a SERS substrate formed in accordance with an embodiment of the present invention.

In one exemplary embodiment, Glass fiber filter papers (Millipore, Billerica, Mass.) were coated with 20-50 µL of Ag nanoparticle printing ink, 40% by weight, (UT Dots, Inc. Champagne, Ill.). The substrates were then heated at 180° C. for 15 minutes. Before use, the substrates were allowed to cool for an additional 15 minutes. FIGS. 9(a)-9(c) show SEM micrographs of the sintering of the Ag nanoparticles that occurs during the heating processes. FIG. 9(a) shows uncoated filter fibers. FIG. 9(b) shows a close up view of a single filter fiber that is covered with Ag nanoparticles 15-20 nm in diameter. FIG. 9(c) is an enlarged view of fractal aggregates of nanoparticles on the surface of a filter fiber The flexible SERS substrate of this example was used to detect Rhodamine (Rh6G) in 0.1 nanomolar concentrations (about 2 molecules of Rh6G per trillion molecules of water). FIG. 11 is a graph showing the Raman spectrum of Rh6G on a flexible SERS substrate formed in accordance with an embodiment of the present invention. The SERS substrate is used as filter to trap the Rh6G in the water. 0.1 nanomolar of Rh6G is clearly detectable by RS with a peak at 1510 $cm^{-1}$.

Example 2

Figure 12:
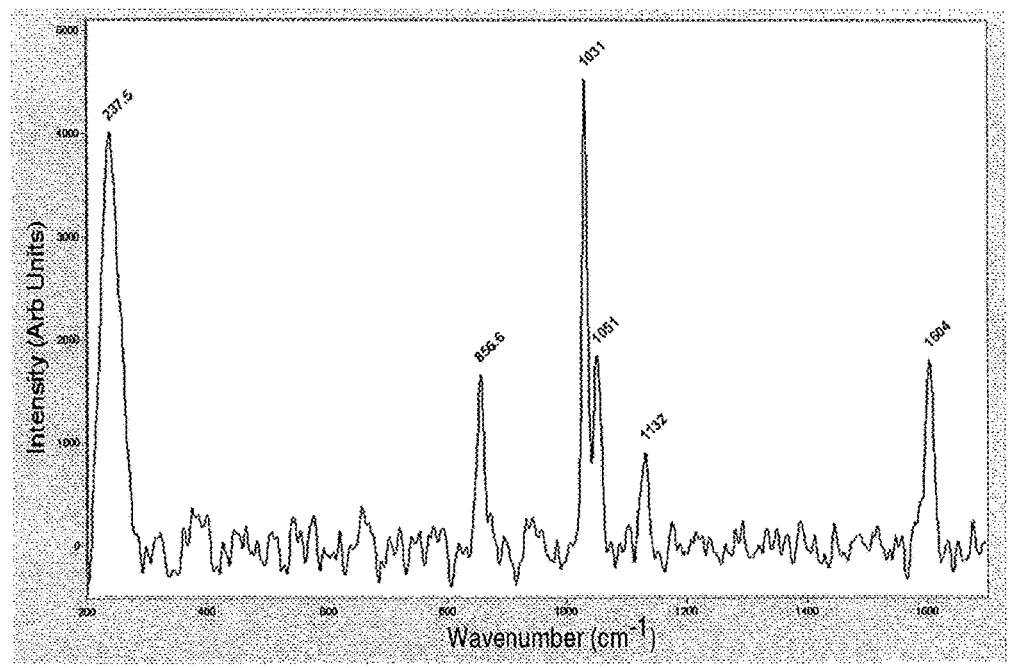
FIG. 12 is a graph showing the Raman scattering spectrum of nicotine on a SERS substrate formed in accordance with an embodiment of the present invention.
Figure 13:
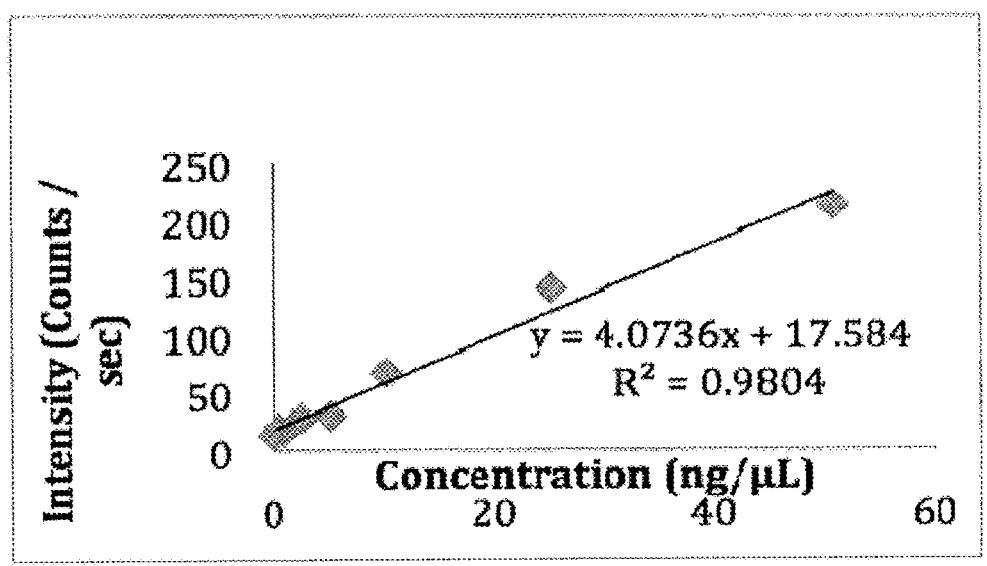
FIG. 13 shows the SERS signal intensities of the nicotine peak at 1032 cm$^{-1}$ at different concentrations of nicotine in 1.0 mM NaCl solution.

The flexible SERS substrate of the present invention was used to detect nicotine from cigarette smoke. As show in FIG. 12, the main peak at 1032 $cm^{-1}$ is for nicotine, which is obtained by mixing smoke from a lit cigarette in a mixing chamber and then drawing the mixture through the SERS filter. Nicotine at concentrations as low as 0.5 molecule per billion air molecules are detectable using the SERS substrate of the present invention. In FIG. 13, the SERS signal for nicotine at 1032 $cm^{-1}$ was detected at concentrations as low as 0.5 ng/µL from a solution diluted with 1.0 mM NaCl.

Example 3

Rhodamine-6G (Rh6G), nicotine solution and sodium chloride were obtained from Fisher Scientific. Cellulose fiber fabric samples were coated with silver nanoparticle printing ink, 40% by weight, (UT Dots, Inc Champagne, Ill.). Substrates were then heated at 180° C. for 15 minutes just before use. The filter substrates were secured on a 2-cm wide opening on one end of a plastic chamber (0.6 m×0.4 m×0.2 m). Albuterol was introduced through an inlet opening on the other side of the chamber. The SERS spectra were collected with an Advantage Near-Infrared Raman Spectrometer (Delta Nu, Laramie, Wyo.) with an excitation wavelength of 785 nm. Microwave absorption measurements were made using a modified X-band Varian E-12 EPR spectrometer with an associated heater accessory.

Figure 14:
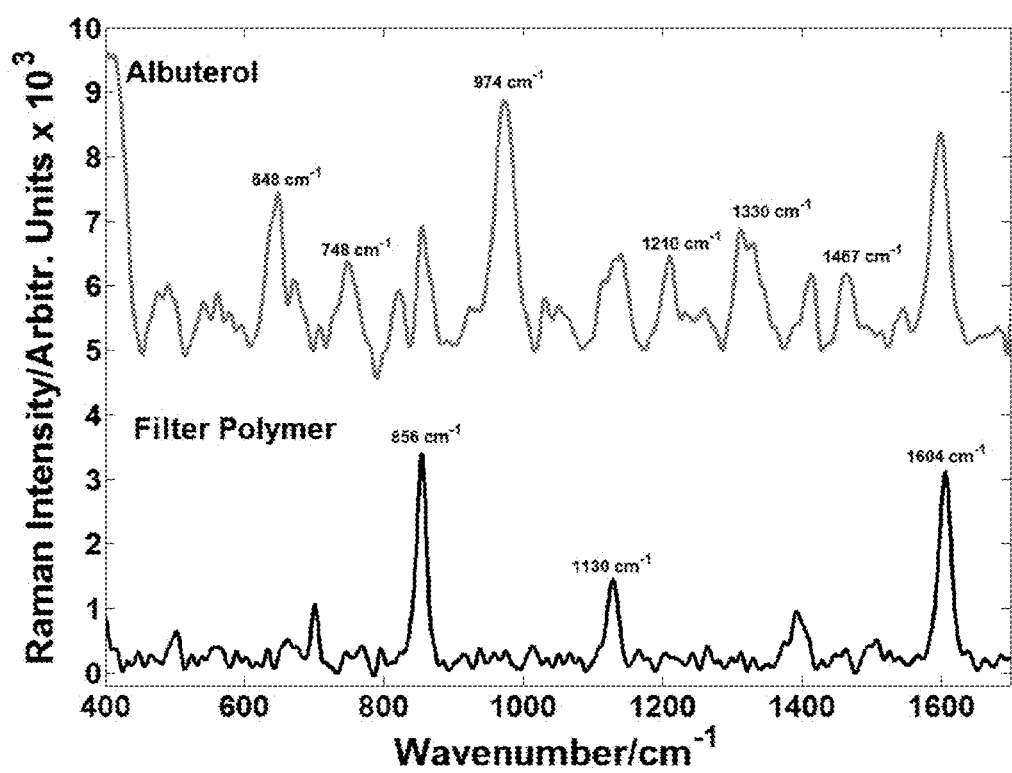
FIG. 14 shows the SERS signal intensities for albuterol sulfate as measured in Example 3, wherein (a) is the albuterol SERS signal and (b) is a background SERS signal from the filter paper substrate.

Albuterol sulfate, also known as salbutamol hemisulphate, is a beta-2 adrenergic bronchodilator found in asthma metered dose inhalers. Each dose delivers 90 micrograms of albuterol sulfate. One actuation of the medicine was introduced into the chamber followed by pumping the air-albuterol mixture out of the chamber through the SERS filter. The actual amount of albuterol trapped by the filter will depend on the porosity of the filter and the flow rate of the air-albuterol mixture through the filter. These parameters were not optimized. The filter was removed for recording SERS signal and detection of the albuterol vibrational bands. The main band between 970 cm$^{-1}$ and 990 cm$^{-1}$ shown in FIG. 14 corresponds to the C—OH group and was used for identification purposes. The other peaks agree well with a recent vibrational spectroscopic study of albuterol. Three other peaks, 856.6 cm$^{-1}$, 1132 cm$^{-1}$ and 1604 cm$^{-1}$, are attributed to a polymer found on the filter paper.

Example 4

Figure 15:
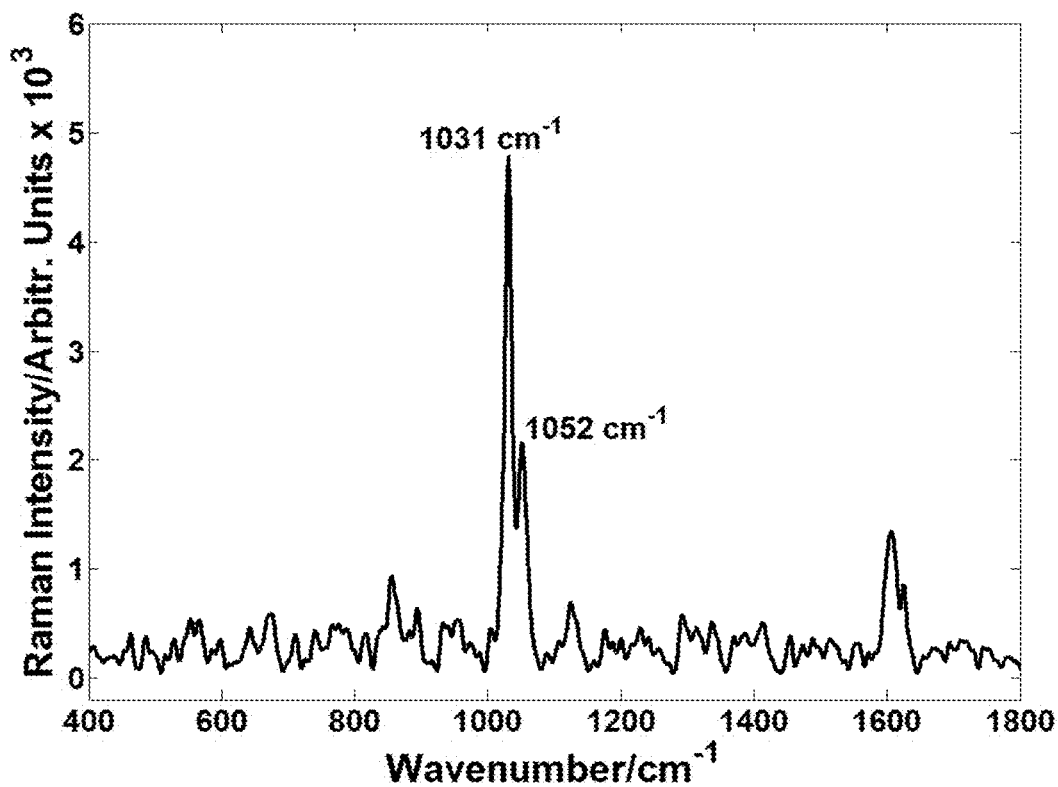
FIG. 15 shows a SERS spectrum obtained from a cigarette smoke-air mixture filtered through the SERS filter as described in Example 4 below. The primary signal for nicotine is seen at 1031 cm$^{-1}$ with the other peaks being attributable to background signal from the filter paper substrate.

The procedure of Example 3 was repeated except that cigarette smoke was introduced through the inlet opening of the chamber instead of albuterol and the cigarette smoke was pumped through the silver-coated SERS filter. FIG. 15 shows a SERS spectrum obtained from the cigarette smoke-air mixture filtered through the SERS filter as described above. A drop of 10 mM NaCl solution was used to increase nicotine adsorption on the SERS substrate before recording the spectrum. The main band in the SERS spectrum of nicotine at 1031 cm$^{-1}$ is attributed to the pyridine-ring breathing mode. Using the signal from a standard nicotine solution, the detection limit for the present SERS substrates was estimated to be 1-2 molecules of nicotine per billion molecules of water.

Example 5

SERS substrates are known to have a limited shelf life since the silver in the substrates tends to oxidize over time, thereby degrading the performance of the SERS substrates. The SERS substrates of the present invention, however, have a relatively long shelf-life due to the encapsulation of the silver nanoparticle inks in polymer shells. The polymer shells are believed to reduce or prevent oxidation of the silver nanoparticles by minimizing or eliminating their exposure to an oxidizing environment. This deterioration of the amplification factor primarily occurs due to a reduced coupling between the analyte molecule and the nanoparticle. The surface quality can also affect the surface plasmon resonance characteristics.

Figure 16:
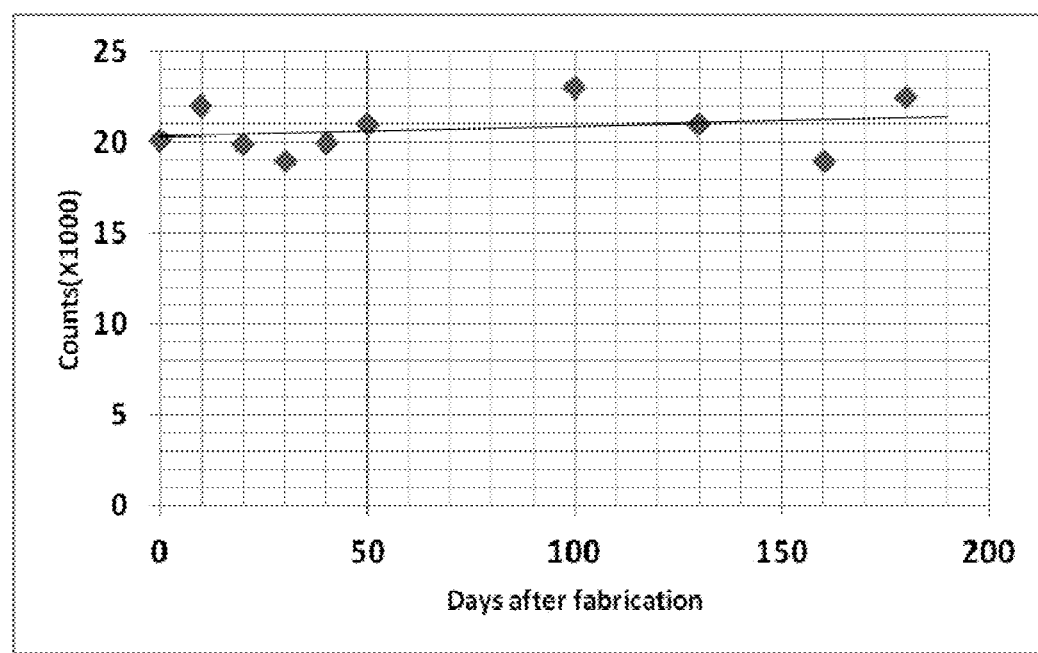
FIG. 16 is a plot of counts (×1000) versus storage time showing at least a 6 month shelf-life for the SERS substrates as tested in Example 5 below.

The polymer coating provides a natural barrier against such deterioration. In this example, SERS substrates in accordance with the present invention were stored for periods of up to about 6 months in a lab dessicator under moderate vacuum. At the time of use, the SERS substrates were activated by subjecting them to a heating treatment. These stored SERS substrates could then be used without any significant degradation of their performance within experimental error of the measurement method, as shown in FIG. 16.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A surface-enhanced Raman spectroscopy substrate comprising:
    a flexible substrate having filtering capability for trapping an analyte of interest on said substrate during filtration of a media containing said analyte and including a material selected from glass fibers, cellulose fibers and polyimide fibers, said flexible substrate having a distribution of nanoparticle cluster sizes and interparticle distances and said flexible substrate providing a three dimensional surface having multiple anchoring sites for an analyte molecule; and
    fractal aggregates of nanoparticles comprising a material which enhances Raman scattering located on a surface of said substrate, wherein said nanoparticles provide an amplification of a Raman scattering signal of from about $1 \times 10^3$ to about $2.5 \times 10^{10}$ relative to a Raman scattering signal of said flexible substrate in the absence of said nanoparticles.

2. The surface-enhanced Raman spectroscopy substrate of claim 1, wherein the nanoparticles comprise a material selected from the group consisting of silver, gold and copper.

3. The surface-enhanced Raman spectroscopy substrate of claim 1, wherein said fractal aggregates of nanoparticles provides an amplification of the Raman scattering signal of from about $6 \times 10^6$ to about $2.5 \times 10^{10}$.

4. The surface-enhanced Raman spectroscopy substrate of claim 1, having a resistivity from about $2.0 \times 10^{-4}$ to $5.0 \times 10^{-4}$ Ω·cm.

5. The surface-enhanced Raman spectroscopy substrate of claim 1, which contains less than 5% of residual stabilizer.

6. The surface-enhanced Raman spectroscopy substrate of claim 1, which contains less than 0.5% of residual stabilizer.

7. A method for detecting an analyte in a large volume sample using a surface-enhanced Raman spectroscopy substrate comprising the steps of:
    forcing said sample through a surface-enhanced Raman spectroscopy substrate as claimed in claim 1 in order to trap the analyte on said substrate;
    exciting the surface-enhanced Raman spectroscopy substrate to cause it to emit light,
    detecting a wavelength of light emitted by said surface-enhance Raman spectroscopy substrate, and
    correlating the detected wavelength of light to the analyte trapped on said substrate.

8. The method of claim 7, wherein a wavelength of from about 480 nm to about 1000 nm is employed for Raman excitation in said exciting step.

9. The method of claim 7, further comprising the steps of:
    measuring an amount of the sample forced through said surface-enhanced Raman scattering substrate,
    determining an area of a peak of detected light at a wavelength of an analyte of interest, and
    calculating a concentration of said analyte in the sample based on said measured amount of sample and the area of the peak.

10. The method of claim 7, wherein said step of forcing sample through said flexible substrate is accomplished by using a pump.

11. The method of claim 7, wherein said sample is pre-filtered before said forcing step to remove large particles.

12. A method of fabricating the flexible-surface enhanced Raman spectroscopy substrate as claimed in claim 1, including steps of:
    applying a nanoparticle ink to a surface of a flexible substrate having filtering capability for trapping an analyst of interest on said substrate during filtration of a media containing said analyte, wherein the nanoparticle ink comprises a liquid vehicle, a plurality of nanoparticles, and a stabilizer;
    heating the nanoparticle ink and the substrate to a suitable temperature for a period of time to remove liquid vehicle and at least some of said stabilizer and form fractal aggregates of nanoparticles on the substrate, wherein said heating step is terminated when an amplification of Raman scattering signal of from about $1\times10^3$ to about $2.5\times10^{10}$ is achieved relative to a Raman scattering signal of said flexible substrate in the absence of said nanoparticles.

* * * * *